United States Patent [19]

Koziol et al.

[11] Patent Number: 4,597,388
[45] Date of Patent: Jul. 1, 1986

[54] APPARATUS FOR REMOVING CATARACTS

[75] Inventors: Jeffrey Koziol, Mt. Prospect; Christopher Nowacki, Arlington Heights; Alfred G. Brisson, Schaumburg, all of Ill.

[73] Assignee: Trutek Research, Inc., Arlington Heights, Ill.

[21] Appl. No.: 561,894

[22] Filed: Dec. 15, 1983

[51] Int. Cl.⁴ .............................................. A61B 17/36
[52] U.S. Cl. .................. 128/303.1; 128/303 R
[58] Field of Search ............. 128/24 A, 303 R, 303.1, 128/328, 395

[56] References Cited

U.S. PATENT DOCUMENTS

| | | | |
|---|---|---|---|
| 2,559,227 | 7/1951 | Rieber | 128/24 A |
| 3,857,387 | 12/1974 | Shock | 128/24 A |
| 3,971,382 | 7/1976 | Krasnov | 128/303.1 |
| 3,982,541 | 9/1976 | L'Esperance, Jr. | 128/395 |
| 4,078,564 | 3/1978 | Spina et al. | 128/303 R |
| 4,164,222 | 8/1979 | Prokhorov et al. | 128/303.1 |
| 4,311,147 | 1/1982 | Hausler | 128/328 |
| 4,396,285 | 8/1983 | Presta et al. | 128/303.1 |
| 4,454,882 | 6/1984 | Takano | 128/303.1 |

FOREIGN PATENT DOCUMENTS

| | | | |
|---|---|---|---|
| 2538960 | 4/1977 | Fed. Rep. of Germany | 128/303.1 |
| 2913251 | 10/1980 | Fed. Rep. of Germany | 128/328 |
| 3146626 | 6/1983 | Fed. Rep. of Germany | 128/328 |
| 0988288 | 1/1983 | U.S.S.R. | 128/303.1 |

Primary Examiner—Kyle L. Howell
Assistant Examiner—Ruth S. Smith
Attorney, Agent, or Firm—Trexler, Bushnell & Wolters, Ltd.

[57] ABSTRACT

A method and apparatus are provided for removing an eye lens having a cataract therein. An electric spark is discharged in a hydraulic medium to cause an electrohydraulic shock which is focused on or directly conducted to the lens, thereby to liquify the lens, which is then readily flushed from position.

5 Claims, 10 Drawing Figures

APPARATUS FOR REMVING CATARACTS

BACKGROUND OF THE INVENTION

The front portion of the eye, and particularly the human eye, comprises a lens, an iris determining the effective diameter of the lens, and a cornea covering the iris and lens. The adult lens is normally clear and includes a relatively hard nucleus surrounded by a relatively soft cortex. Some lenses ultimately become partially or totally opaque, the opacity being known as a cataract.

The treatment of a cataract presently involves removal of the cataract from the eye by surgical means. There are presently three different techniques used for cataract surgery. The first is called intracapsular cataract surgery. In this method, an incision from 12-15 mm is made into the eye and the entire lens, including capsule, cortex and nucleus is removed en bloc. The second is called extracapsular cataract surgery. In this method an incision of 10-12 mm is made and the lens removed in pieces leaving the posterior capsule inside the eye. This method has been gaining in popularity because it makes use of the posterior capsule to support an intraocular lens. The third is called phakoemulsification. In this method, a 3 mm incision is made and the lens removed in pieces. The relatively large hard nucleus (8-11 mm in diameter) is removed through a 3 mm incision by use of an ultrasonic vibrating tip that is inserted inside the eye. When this tip is brought in contact with the hard nucleus the nucleus is shattered by direct contact with the rapidly vibrating tip. The method can be associated with high complication as the ultrasonic tip can permanently damage portions of the eye, such as the cornea when such a portion is contacted.

OBJECTS AND SUMMARY OF THE PRESENT INVENTION

It is the object of the present invention to provide an instrument that will soften or liquify the nucleus of a cataract from outside the eye. This will permit removal of a cataract through a small incision (3 mm or less) and reduce the possibility of eye damage when a high frequency ultrasonic probe is inserted inside the eye.

More particularly, it is an object of the present invention to provide an apparatus for liquifying the lens of an eye having a cataract therein so that the lens may be simply flushed from position without damage to adjacent tissue.

In achieving the foregoing and other objects of the present invention we provide a shock wave focused on the lens and specifically within the nucleus thereof to cause a localized shock or succession of shocks which reduce the lens to a liquid. More particularly, we provide a spark gap in a liquid, for example, a saline solution. The spark formed in the gap is of high energy and vaporizes the water between the electrodes defining the spark gap. The water moves very quickly to move out of the way of the vapor. This causes a substantial physical shock which travels rapidly through the saline solution. The saline solution in question can be that which is normally used during eye surgery. To insure focusing of the shock wave within the lens nucleus we provide a pair of laser aiming beams which cross at the precise point of focus. As is known, lasers produce coherent light beams with no scatter, whereby the precise point of focus can readily be seen. The liquified lens is aspirated from the eye.

THE DRAWINGS

The present invention will best be understood from the following description when taken in connection with the accompanying drawings wherein:

FIG. 1 comprises a somewhat schematic longitudinal sectional view through the apparatus of the present invention as applied to an eye;

DETAILED DESCRIPTION OF THE ILLUSTRATED EMBODIMENT

Figure 1:
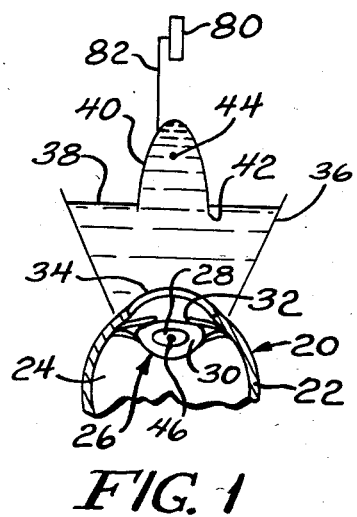

Referring now in greater particularity to the drawings, and first to FIG. 1, there will be seen a representation in cross section of the forward portion of an upwardly facing eye 20 including the sclera 22 and the vitreous body 24. The eye includes a lens 26 having a nucleus 28 of generally hard material, and a surrounding cortex 30 of relatively soft material. An iris 32 partially overlies the lens, the lens and iris being supported by suitable surrounding tissue. A cornea 34 covers the lens and iris.

As further may be seen in FIG. 1 there is provided for ophthalmic surgery an upwardly flaring, frusto-conical bottomless vessel 36 having a suitable aqueous solution 38 therein. Commonly this aqueous solution is a saline solution, but it is contemplated that other liquids could be used. The open bottom engages the forward portion of the eye so that surgery may be carried out on the cornea and lens under the liquid solution.

In accordance with the present invention a reflector 40 (see also FIG. 3) is provided having the lower edge 42 thereof below the top of the liquid 38. In accordance with a preferred example of the invention the reflector 40 is a portion of an ellipsoid, this geometric solid figure being chosen because it has two focal points. In FIG. 1, the first focal point 44 is within the confines of the reflector, while the second focal point 46 is centered within the nucleus 28 of the lens. A wave that appears at one focal point, for example the focal point 44, is focused at the second focal point 46.

Figure 3:
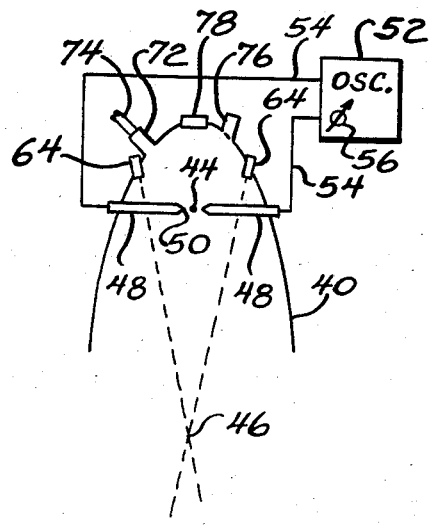
FIG. 3 is a somewhat schematic enlarged sectional view showing details omitted from FIG. 1.

Inventive details of the present invention will be seen in FIG. 3 wherein a pair of electrodes 48 is shown supported by the reflector 40 in diametral relation to one another providing a spark gap 50 across the focal point 44. The reflector 40 may be made of metal, in which case the electrodes are insulated therefrom, but it is also contemplated that the reflector 40 could be made of insulating plastic, in which case specific insulation for the electrodes would not be needed. The electrodes are supplied with energy from a high voltage pulse generator 52 over connecting wires 54 including internal spark gaps 55 (FIG. 5), the generator having an adjustment as indicated at 56. The internal spark gaps 55 eliminate a DC circuit which could cause damage if the spark gap 50 were short circuited, and insure constant power to spark gap 50.

Figure 5:
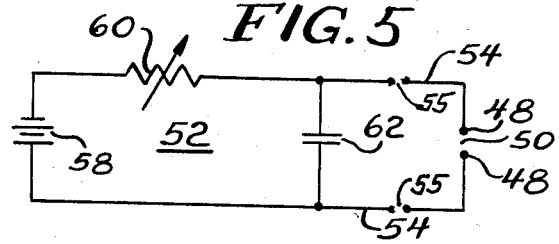
FIG. 5 is a schematic view of an oscillator circuit used in the present invention.

Additional details of the pulse generator can be seen in FIG. 5, and the generator is conveniently a relaxation oscillator. Power is supplied from a suitable direct current electric source indicated as a battery 58 through a variable resistor 60 to charge a capacitor 62. The electrodes 48 and spark gap 50 are in parallel with the capacitor 62. The capacitor charges at a predetermined rate through the resistor 60 until there is enough voltage on the capacitor to break down the spark gap 50, whereupon the capacitor discharges across the spark gap.

The amount of energy being dissipated across the spark gap can be adjusted in at least three ways. These include the distance across the spark gap, the voltage across the capacitor, and the pulse repetition rate. The illustrative example utilizes a variable resistor and hence a variable pulse repetition rate, as this is the simplest to realize.

Returning to FIG. 3, laser sources 64 extend through the shell of the reflector 40 relatively toward the top thereof, and are aimed toward the second focal point 46. These are used for visual aiming and positioning of the reflector to insure that the focal points 44 and 46 are properly oriented relative to one another to cause the shock wave generated by the spark across the gap 50 concentrating on the focal point 46. Preferably the laser sources 64 are rotated 90 degrees about the longitudinal axis of the reflector 40 relative to the electrodes 48 to minimize interference, although they are shown in the same plane in FIG. 3 for convenience.

Figure 4:
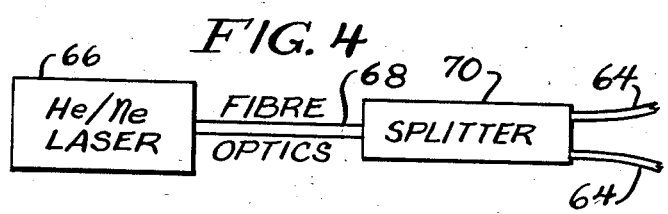
FIG. 4 is a schematic view illustrating utilization of a laser in the present invention.

One laser arrangement is shown in FIG. 4 wherein there is a helium/neon laser 66 connected through fiber optics 68 to a splitter 70. The splitter has two bundles of fiber optics extending therefrom, respectively comprising the laser sources 64 of FIG. 3.

Again, returning to FIG. 3, there will be seen a fluid fitting 72 connected to a flexible tubing 74 leading to a vacuum source, and thereby to pull fluid from the bath 38 up into the reflector 40, and substantially to fill the reflector. The fluid fitting 72 would be as close to the apex of the reflector 40 as possible, and the reflector would be slightly rocked when withdrawing air to insure filling the reflector as nearly as possible with the aqueous solution 38.

A white light source 76 is provided relatively near the apex of the reflector to provide visible light at the lens 26 to illuminate the work area of the ophthalmic surgeon. This light would preferably be in the same plane as the laser sources 64 to minimize interference with the electrodes 48.

Finally, at the apex of the reflector there is provided an optically transparent element 78 for viewing of the eye lens by the ophthalmic surgeon. To avoid fracturing of the element 78 by the shock generated by the spark gap it is preferred that the element 78 be an elastomeric substance such as a silicone. As shown in FIG. 1 an ophthalmic microscope 80 would be positioned externally of the reflector, supported by support 82 from the reflector so that the microscope will move with the reflector. The ophthalmic surgeon thus has a clear view through the microscope and through the transparent element 78 and the spark gap down to the eye lens 26.

Figure 2A:
FIG. 2A shows a modification of the positioning of the microscope used in the proceedure.
Figure 2B:
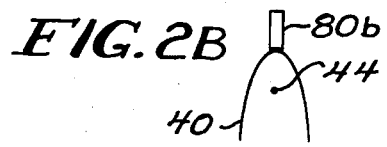
FIG. 2B is a schematic view similar to 2A showing another position for the microscope.

Alternative arrangements of the microscope are shown in FIGS. 2A and 2B. In FIG. 2A the microscope 80A is supported by a support 82A to one side of the reflector 40 and near the leading edge thereof for viewing of the eye lens without having to sight through the reflector. The lower end of the microscope 80A would be beneath the surface of the aqueous solution 38 to avoid problems of surface reflections and refraction at the surface. In FIG. 2B the microscope 80B is mounted directly on the apex of the reflector 40 on top of the transparent element 78.

Figure 6:
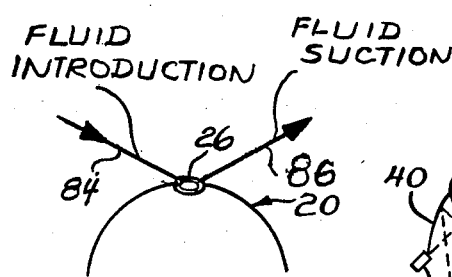
FIG. 6 is a somewhat schematic view showing flushing of the liquidized lens from place.

Each time a spark jumps the gap 50 between electrodes 48 there is a discharge of high energy which vaporizes the water between the electrodes. The water moves very quickly to move out of the way of the vapor in perhaps one microsecond. The spark recurs frequently, illustratively in the range of once per second to one hundred per second, thus setting up a series of electro-hydraulic shock waves focused on the focal point 46 within the nucleus of the lens 26. The laser beams allow visual aiming to insure that the second focal point 46 will be within the nucleus of the lens. The repeating hydro-electric shock causes the hard nucleus of the lens to break-up or liquify so that the entire lens may be flushed from place. The eye 20 is shown figuratively in FIG. 6, the lens being at 26. A known coaxial hydraulic irrigation device introduces fluid to the lens at 84, while a fluid suction is established at 86 to remove the fractured or liquified portions of the lens. It will be understood that during this proceedure a corneal scleral incision is made and an irrigating aspirating instrument inserted inside the eye as it is in conventional extracapsular cataract surgery. In a matter of seconds or a few minutes, the entire lens may be fragmented or liquified and flushed away by the proceedure just described. Since the energy is concentrated within the lens, little or no damage or shock is imparted to adjacent portions of the eye whereby a new lens may be implanted under ideal conditions. Since a small incision is made, healing and adapting to the new lens are remarkably quick.

Figures 7, 8:
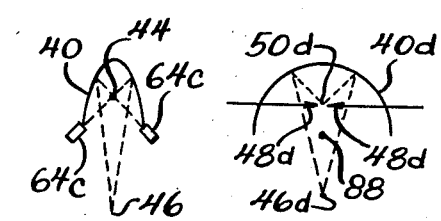
FIG. 7 is a schematic longitudinal sectional view showing an improved utilization of the laser beams.
FIG. 8 is a further longitudinal schematic view showing a different type of reflector.
Figure 9:
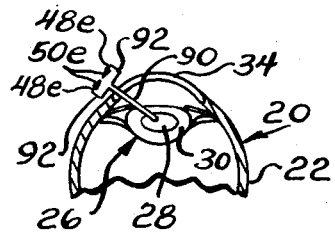
FIG. 9 is a fragmentary longitudinal sectional view similar to part of FIG. 1 showing mechanical application of shock wave to the lens.

Variations of certain details of the invention are shown in FIGS. 7–9. In FIG. 7, the laser sources 64C are aimed at the first focal point 44 of the reflector 40 insuring that the laser beam is coincident with the local point of the ellipsoid. The rays passing through the focus point 44 will be reflected from the inside of the reflector 40 to the lower focus point 46 for aiming of the apparatus. The reflected rays are shown in highly idealized fashion in FIG. 7 as straight line paths, rather than multiple reflecting paths which would tend to obscure the principles.

In FIG. 8 there is a different reflector, this reflector 40D being spherical in nature. The spark gap 50D between the electrodes 48D is positioned above the center of radius 88 of the reflector to focus on the location 46D within the nucleus of the lens.

In the embodiment of the invention illustrated in FIG. 9 there is no reflector and no aqueous propagation of shock waves. Rather, a rigid probe 90 has the end thereof extending directly into the nucleus 28 of the lens 26 approximately at the center there. The electrodes 48e are mounted rigidly on the end of the probe 90 by means of rigid supports 92. The shock wave generated upon jumping of the gap by a spark thus is transmitted directly and physically through the probe 90 into the eye lens 26. The probe preferably would be supported from a suitable base (not shown) by a support resiliently holding the probe 90 so as to avoid damping the shock waves therein. It will be understood that the electrode 48e and the spark gap 92 are beneath the surtace of the aqueous solutuion 38 in the vessel 36.

The invention forming the subject matter of the present application should now be understood. As previously has been noted a saline solution is used in the practice of the invention. This is not the normal saline solution, as it is too conductive. It is preferred that a saline solution of one/half to one/quarter normal be used. It is also contemplated that a glucose or dextrose solutuion could be used. A certain amount of conductivity is necessary, and the liquid medium must be non-compressible for the shock wave to work properly. It is also contemplated that the aqueous solution within the relfector could be supplanted by a soft silicone mass. There would be no liquid as such except for a small bubble around the spark gap to institute the shock wave.

Although the reflector could be made of metal, it is preferred that it be molded of plastic and that the entire assembly of reflector, electrodes, laser sources, white light and suction be disposable as re-sterilization after use would be difficult. It is to be understood that various parts in the drawings are not necessarily to scale, and for example the reflector could have a two inch diameter which would make it larger relative to the eye than shown in FIG. 1. It is also contemplated that the front edge of the reflector would be approximately one inch from the front of the eye or less. The normal eye lens in a human being is about 2 and one/half millimeters in diameter, and it is contemplated that the source, i.e., the reflector and attached parts would be moved around somewhat during use to liquify the entire lens.

While reference is made throughout to removal of a lens having a cataract therein, it will be understood that the process and apparatus of the present invention are equally applicable to removal of a lens for any other medical reason, and the claims are to be so construed.

The specific embodiments of the invention as herein shown and described are for illustrative purposes only. Various changes in structure will no doubt occur to those skilled in the art and will be understood as forming a part of the present invention insofar as they fall within the spirt and scope of the appended claims.

The invention is claimed as follows:

1. Apparatus for removing an eye lens comprising hydraulic fluid, means for supporting said hydraulic fluid on the eye, means for generating a shock wave in said hydraulic fluid, means for focusing said shock wave comprising reflector means to apply said shock wave through said hydraulic fluid to the lens of said eye to liquify said lens, said reflector means including a portion of an ellipsoid having a first focal point within said reflector means and a second focal point outside of said reflector means, said reflector means being movable to position said second focal point within said lens, the means for generating a shock wave generating said shock wave at the first focal point, and three dimensional aiming means, comprising intersecting laser beams, connected to said reflector means and aimed at said second focal point for locating said second focal point within said lens.

2. Apparatus as set forth in claim 1 and further including means for mounting an ophthalmic microscope relative to said reflector.

3. Apparatus as set forth in claim 1 and further including means for illuminating said lens supported from said reflector.

4. Apparatus as set forth in claim 1 wherein the means for generating a shock wave comprises a spark gap.

5. Apparatus as set forth in claim 1 and further including means for flushing away the liquified lens.

* * * * *